United States Patent [19]

Van der Knaap

[11] Patent Number: Plant 6,301

[45] Date of Patent: Sep. 20, 1988

[54] CHRYSANTHEMUM PLANT NAMED YELLOW CASSA

[75] Inventor: Jacques C. M. Van der Knaap, De Lier, Netherlands

[73] Assignee: Fides Beheer B.V., De Lier, Netherlands

[21] Appl. No.: 915,105

[22] Filed: Oct. 3, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Yellow Cassa particularly characterized by its flat capitulum form and single daisy capitulum type; yellow ray floret color; diameter across the face of the capitulum of 40≠60 mm; vigorous growth habit, and its green to yellow-orange disc florets.

1 Drawing Sheet

The present invention comprises a new and distinct cultivar of Chrysanthemum, botanically known as *Chrysanthemum morifolium.*, Ramat., and referred to by the cultivar name Yellow Cassa.

Yellow Cassa was discovered in 1981 by applicant as a spontaneous mutation of Cassa, a cultivar of applicant disclossed in a pending application.

Yellow Cassa was the result of an induced radiation program conducted by applicant in De Lier, The Netherlands, in 1981. Plants of the parent cultivar Cassa were subjected to radiation levels of 1750 rad X-rays. Yellow Cassa was discovered and selected as a mutation by virtue of its yellow ray floret color, as opposed to the white ray floret color of Cassa. During trialing and development of Yellow Cassa, it was also noted that the new cultivar is more vigorous than its parent.

The first act of asexual reproduction of Yellow Cassa was accomplished when vegetative cuttings were taken from the initial selection in 1981 in a controlled environment in De Lier, The Netherlands by a technician working under formulations established and supervised by Jacques C. M. Van der Knaap. Horticultural examination of selected units initiated in 1981 has demonstrated that the combination of characteristics as herein disclosed for Yellow Cassa are firmly fixed and are retained through successive generations of asexual reproduction.

Yellow Cassa has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Yellow Cassa which, in combination, distinguish this Chrysanthemum as a new and distinct cultivar:

1. Flat capitulum form.
2. Single daisy capitulum type.
3. Bright yellow ray floret color.
4. Diameter across the face of the capitulum 40–60 mm.
5. Yellow-green (immature) to yellow-orange (mature) disc florets.

6. Vigorous growth habit, particularly when compared with the parent cultivar Cassa.

Of the many commercial cultivars known to the present inventor, the most similar in comparison to Yellow Cassa is the parent cultivar Cassa. The new cultivar differs from Cassa only in flower color and increased vigor.

The accompanying photographic drawing shows typical inflorescence and foliage characteristics of Yellow Cassa, with the colors being depicted as accurately as possible with photographs of this type.

In the following description, color references are made to The Royal Horticultural Society Colour Chart. The color values were determined in August 1986 under natural daylight at De Lier, The Netherlands.

Classification:

*Botanical.*—*Chrysanthemum morifolium.*, Ramat., cv. Yellow Cassa.

*Commercial.*—Cut daisy spray.

INFLORESCENCE

A. Capitulum:
- *Form.*—Flat.
- *Type.*—Daisy.
- *Diameter across face.*—40–60 mm.

B. Corolla of ray florets:
- *Color (general tonality from a distance of three meters).*—Yellow.
- *Color (upper surface).*—6D.
- *Color (under surface).*—4D.

C. Corolla of disc florets:
- *Color (mature).*—Yellow-orange 14A.
- *Color (immature).*—Green 166B.

D. Reproductive organs:
- *Androecium.*—Present in disc florets; numerous.
- *Gynoecium.*—Present in both ray and disc florets; numerous.

PLANT

A. General appearance:
- *Height.*—80 cm.

B. Foliage:
- *Color (upper surface).*—147B.
- *Color (under surface).*—147A.
- *Shape.*—Short lobed and finely serrated.

C. Growth habit: Vigorous.

We claim:

1. A new and distinct Chrysanthemum plant named Yellow Cassa, as described and illustrated, and particularly characterized by its flat capitulum form and single daisy capitulum type; yellow ray floret color; diameter across the face of the capitulum of 40–60 mm; vigorous growth habit, and its green to yellow-orange disc florets.

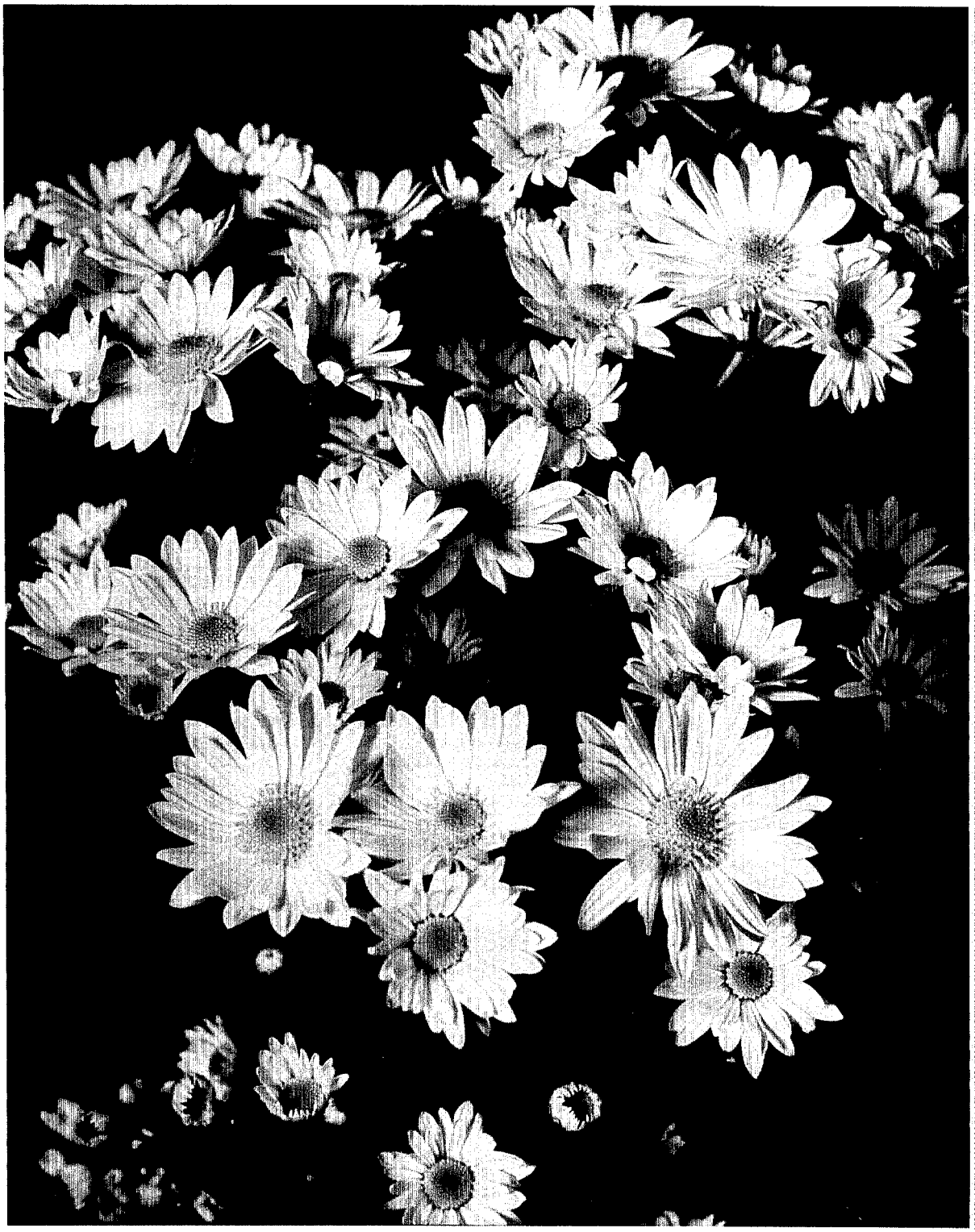

* * * * *